United States Patent [19]

Swedo et al.

[11] Patent Number: 4,815,445
[45] Date of Patent: Mar. 28, 1989

[54] SOLID CATALYSTS FOR EPIMERIZATION OF ALDOSES; CONTINUOUS INTERCONVERSION OF EPIMERIC SUGARS

[75] Inventors: Raymond J. Swedo, Mt. Prospect; Blaise J. Arena, Des Plaines; Bruce E. Firth, Arlington Heights, all of Ill.

[73] Assignee: Allied-Signal Inc., Morristown, N.J.

[21] Appl. No.: 153,866

[22] Filed: Feb. 9, 1988

[51] Int. Cl.$^4$ ............................ C13K 1/00; C13K 13/00
[52] U.S. Cl. ............................ 127/46.1; 536/1.1; 536/124; 127/46.2
[58] Field of Search ............ 127/46.1, 46.2, 46.3; 536/1, 124

[56] References Cited

U.S. PATENT DOCUMENTS

| | | | |
|---|---|---|---|
| 4,029,878 | 6/1977 | Kruse | 536/1 |
| 4,718,405 | 1/1988 | Firth et al. | 127/46.1 |

FOREIGN PATENT DOCUMENTS 55-76894  6/1980  Japan.

OTHER PUBLICATIONS

Bilik & Coworkers, *Chem. Abstract*, 89, (19), 163846 (1978).
Hayes et al., *J. Amer. Chem. Soc.*, 104, 6764 (1982).

*Primary Examiner*—Asok Pal
*Assistant Examiner*—Chung K. Pak
*Attorney, Agent, or Firm*—Harold N. Wells; Thomas K. McBride; Eugene I. Snyder

[57] ABSTRACT

Anion exchange resins which have been exchanged with molybdate at acid pH are effective catalysts for epimerizing compounds with the structural unit:

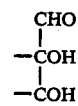

Cheif among these are aldoses, especially aldopentoses and aldohexoses, as well as some deoxy-sugars. A method for the continuous epimerization of aldoses and other compounds having the necessary structural feature shown using a fixed bed of molybdate-exchanged resin is quite efficient, and can be employed in enhancing the yield of the thermodynamically formed epimer which is produced as the minor epimer in a mixture under kinetic control.

16 Claims, 5 Drawing Sheets

SOLID CATALYSTS FOR EPIMERIZATION OF ALDOSES; CONTINUOUS INTERCONVERSION OF EPIMERIC SUGARS

BACKGROUND OF THE INVENTION

The invention discussed and claimed within relates to the epimerization of sugars, and in particular epimerization of aldoses. Even more particularly it relates to solid catalysts which effect such epimerization under relatively mild condition, to the use of such catalysts in epimerizing aldoses, and to a continuous process of epimerizing sugars using a fixed bed of such catalysts.

Recently Bilik in Czechoslovak Certificate of Authorship No. 149,463 has reported that molybodic acid epimerizes aqueous solutions of L-mannose. Reactions conducted at 70° to 95° C. and a pH up to 7 were said to afford equilibrium mixtures of epimeric sugars within a reasonable time. However, Bilik later observed that the epimerization rate of mannose was 20 times slower at pH 5.9 than at 2.9, and that for glucose was 5 times slower, demonstrating that a highly acidic medium is desirable for the epimerization; Bilik and coworkers, Chem. Abst., 89(19): 163846m (1978). Independently we have observed that a highly acidic medium of pH between about 1 and 3 is necessary to effect epimerization at a reasonable rate with amounts of soluble molybdate under about 1500 ppm relative to aldose. U.S. Pat. No. 4,718,405. The latter limitation on the amount of soluble molybdate used is a consequence of commercial reality. Mechanistic studies on the epimerization have been performed by Hayes et al. (J. Amer. Chem. Soc., 104,6764 (1982)) in aqueous solution at a pH of 4.5 and at 90° C. using approximately 30,000 ppm soluble molybdenum relative to aldose.

The procedure of Bilik is valuable insofar as it epimerizes aldoses to an equilibrium mixture without the formation of substantial amounts of byproducts, including color bodies. The epimerization of aldoses is desirable not only in the preparation of relatively rare sugars, such as L-ribose from L-arabinose and 6-deoxy-L-glucose from L-rhamnose, but also in altering the product mixture in sugar syntheses. For example, L-sugars, including L-glucose, have potential as non-nutritive sweeteners, and the preparation of L-glucose is attended by formation of L-mannose. Although separation of L-glucose from L-mannose can be effected in various ways, the presence of mannose in the separation feedstock increases the cost of the purified L-glucose, with its cost increasing with increasing mannose content in the feedstock. Unfortunately, a mixture of L-glucose and L-mannose generally is produced under kinetic control with the L-mannose in preponderance, which imposes heavy cost penalties upon the production of relatively pure L-glucose. Since glucose is thermodynamically favored relative to mannose (Hayes et al.,op. cit.) it follows that if the separated mannose or the kinetically formed product were equilibrated substantial and quite significant reductions it cost would accrue.

However valuable may be the use of soluble molybdate as an epimerizing reagent it still presents stubborn disadvantages in a commercial process. In particular, soluble molybdate requires as a practical matter highly acidic (pH less than about 3.0) solutions for epimerization. Depending on the aldose epimeric pair such a low pH can be vexing in causing side reactions affording unwanted products. The use of a soluble molybdate as an epimerizing reagent also requires an additional processing step to later remove it from solution. Where the epimeric pair is separated frequently it is necessary to remove the molybdate prior to the separation stage, but in any event it would be quite unusual for any industrial use of an aldose to tolerate significant amounts of molybdate in the product. Finally, the use of a soluble molybdate makes it difficult to tailor a continuous epimerization process which often is preferable to a batch process.

What is needed is an epimerization catalyst which operates under heterogeneous reaction conditions, i.e., a solid epimerization catalyst. What is needed is a solid epimerization catalyst which operates at a pH indigenous to aqueous solutions of aldoses, which is normally in the pH range of 4–6. What is needed is a solid epimerization catalyst which remains stable while exhibiting activity at a mildly acidic pH. What is needed is a stable, selective epimerization catalyst operative under only mildly acidic conditions and whose active component is not leached from the catalyst to any significant extent under normal reaction conditions. What we provide is just such a catalyst.

In particular, we have found that strong anion exchange resins whose exchangeable sites are occupied by molybdate are quite active in epimerizing aldoses with high selectivity under mildly acidic conditions. Quite surprisingly, solid catalysts can be made from which less than 50 ppm molybdenum, and often under 10 ppm molybdenum, leached into the epimerized aqueous mixture. The activity of such catalysts in continuous operation remains high through more than 320 hrs. of operation. A process for continuous epimerization based on such solid catalysts is readily devised, successfully practiced, and is economically rewarding, and has the further advantage of effecting isomerization at a pH indigenous to the aqueous solutions of the aldose being isomerized, leading to reduced incidence of undesired side reactions and byproducts.

The low level of molybdenum leach from a solid epimerization catalyst as attained in our invention is an indispensable prerequisite for commercial acceptability of such a catalyst and for commercial success of a continuous epimerization process based on such a catalyst. At the low leach levels characteristic of our process it may not be necessary to require a separate step for molybdenum removal, thereby obviating a unit process in a manufacturing procedure. Although a low molybdenum leach level does not per se ensure prolonged catalyst life, a low leach level is a necessary requirement for high catalyst life with low activity loss since continued removal of molybdenum from the catalyst is tantamount to continued removal of the catalytically active species which must invariably lead to deterioration of catalyst performance.

In U.S. Pat. No. 4,029,878 Kruse disclosed that mannose yield in the epimerization of glucose with a hexavalent molybdenum catalyst is enhanced by using a solution containing at least 50% by weight glucose. The patentee typically used a solution of hexavalent molybdenum at a concentration of at least 0.125 weight percent molybdic acid, and added a mixed bed ion exchange resin after reaction was complete, presumably to remove, or reduce, soluble molybdenum. However, in two cases extraordinarily high levels of molybdic acid (0.83 and 1.67 weight percent) were used in conjunction with an anion exchange resin, but in these cases mannose yield appear less than what could be expected to be observed in the absence of the resin.

In Japanese laid-open application No. 55-76894, the inventors found that an epimerization catalyst of molybdenum-exchanged anion exchange resin identical to that of Kruse rapidly lost activity, their data showing that mannose yields at 90° C. dropped from 30% to under 15% within 35 hours. Largely as a result of this rapid deactivation the workers developed "Mo-type ion-exchange fibers" which could be used as an epimerization catalyst. The nature of this catalyst is not clear. However, a distinction which will be seen to be critical is that these workers exchanged molybdenum under basic conditions, whereas in the present invention it will be seen to be essential to perform the exchange at a rather acidic pH. Although the paucity of description makes the nature of their catalyst and process uncertain, what does seem certain is that the Japanese process fails to demonstrate the low Mo leach levels or the high stability of our catalyst, both essential features of our process.

SUMMARY OF THE INVENTION

A purpose of this invention is to develop a solid catalyst which epimerizes aldoses under heterogeneous conditions. Another purpose is to develop a continuous process for the epimerization of aldoses. An embodiment of a solid epimerization catalyst comprises anion exchange resins in which sufficient sites have been exchanged with a molybdate to afford from about 5% to about 30% by weight molybdenum based on the final resin. In a more specific embodiment the molybdate is exchanged at a pH between about 0.5 and about 6.0. In yet another embodiment an aqueous solution containing at least 1 aldose is epimerized by passing the solution through a fixed bed of a molybdate-exchanged resin at a pH between about 4 and about 6. Other embodiments will be apparent from the ensuring description.

DESCRIPTION OF THE INVENTION

Figure 1:
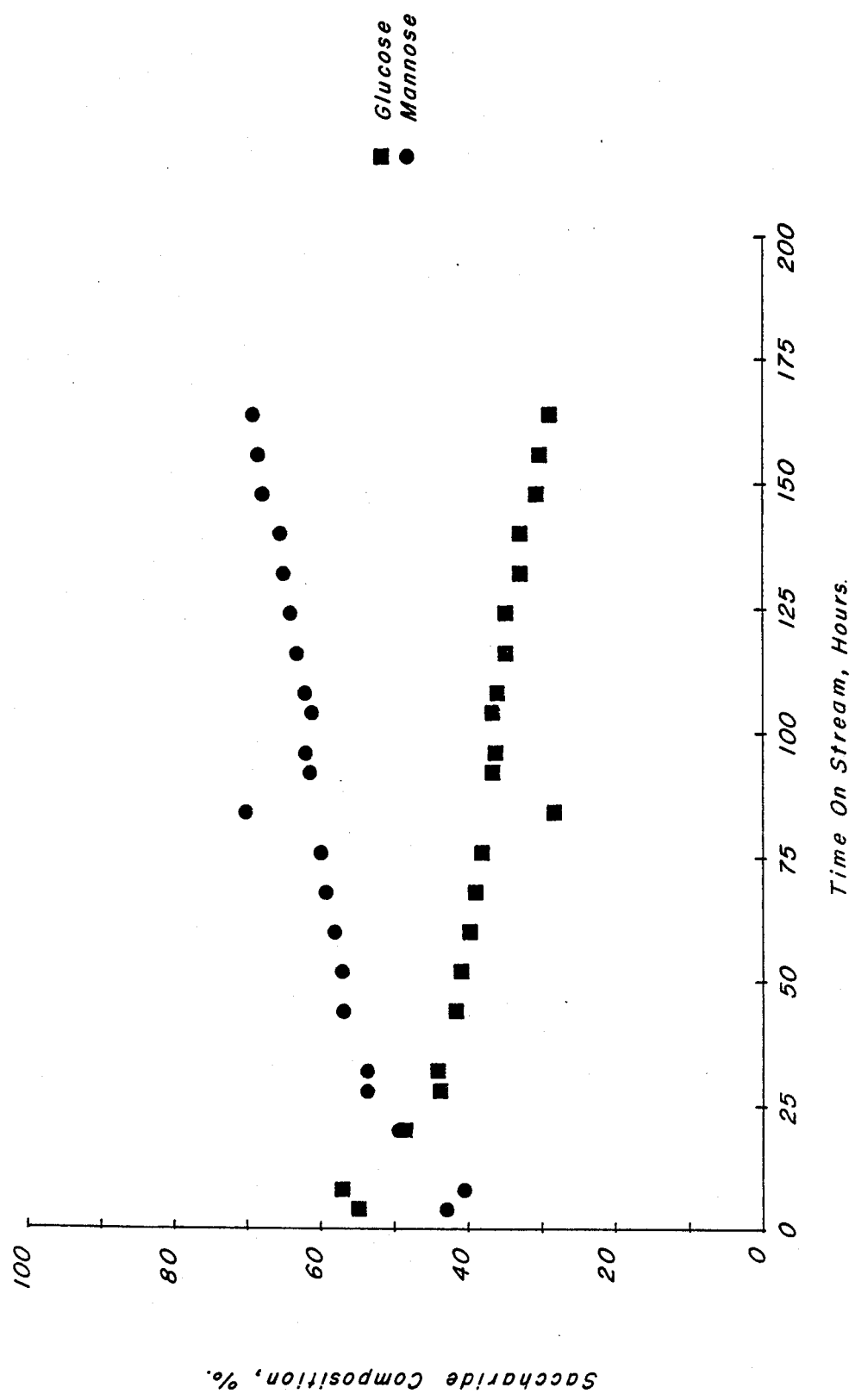
FIG. 1 is a graphical representation of the continuous epimerization of mannose of Example XXII.

This invention is based on our observation that anion exchange resins, especially strong anion exchange resins, which have been exchanged with molybdate under particular conditions afford a solid which acts as an effective epimerization catalyst for aqueous solutions of aldoses at a pH indigenous to such solutions. The solid catalyzes epimerization quite selectively, at reasonable rates, with quite low levels of molybdenum leach, and maintains its activity in continuous use for long periods of time.

The reactants or feedstocks in the epimerization reaction are solutions, generally aqueous solutions, containing at least one aldose or aldose analog. An aldose is a carbohydrate containing an aldehyde group. Those with 4 carbons are called tetroses, those with 5 carbons are called pepntoses, those with 6 are called hexoses, those with 7 heptoses, and so forth. The tetroses consist of erythrose and threose. Included in the pentoses are ribose, arabinose, xylose, and lyxose. The hexoses contain allose, altrose, glucose, mannose, gulose, idose, galactose, and talose. Although the aldohexoses as a group may be the most important, the epimeric aldopentoses, ribose and arabinose, are also important in the practice of this invention.

It is believed (Hayes et al.,op. cit.) that the essential structural unit for epimerization by molybdate is,

and any compound, other than an aldose itself, with such a unit may be called an aldose analog. One class of aldose analogs consists of n-deoxy-aldoses where $n \geq 4$, i.e., aldoses whose hydroxyl group at carbon number n, C-n, (where the aldehydic carbon is C-1) has been replaced by a hydrogen. This class is exemplified by rhamnose, 6-deoxy-glucose, 4-deoxy-lyxose, 5-deoxy-arabinose, 4-deoxy-mannose, and 5-deoxy-talose. Another class includes aldose esters and ketals where ester and/or ketal formation occurs at C-n, with $n \geq 4$. Examples include glucose-6-acetate, mannose-5, 6-dibutyrate, 4,6-0-ethylidene-mannose, and so forth. Yet another class is that of the uronic acids, i.e., hexoses whose hydroxymethyl at C-6 has been converted to the carboxylic acid group.

The concentration of the aldose or aldose analog in solution is not important in the practice of this invention, although as a practical consideration it is advantageous to have the solutions as concentrated as possible consistent with viscosity requirements. It will be recognized that productivity, in the context of the quantity of aldose or aldose analog epimerized per unit time, increases with the concentration of aldose in solution, at least in principle. As a matter of practice solutions from between about 5 to about 50 weight-volume percent are commonly employed. The aqueous solution also may contain other materials, such as additives to prevent growth of bacteria, molds, and so on, such as sulfite or bisulfite salts. The solutions also may contain buffers as well as acid or base to adjust the pH to the desired value. It is most often desired to have a feedstock epimerized at a pH indigenous to the solution, which commonly is between pH about 4 and about 6, even more often in the range between about 4.5 and about 5.0, but if desired epimerization may be effected over the pH range of about 1 to about 6.

The solid epimerization catalyst is an anion exchange resin, and especially a strong anion exchange resin, which has been exchanged with molybdate over a particular pH range. The anion exchange resin may be of the gel or macroreticular type, with its particular nature not being of special significance. Most commonly and preferably the anion exchange resin will be an amine resin of the quaternary ammonium type. Resins which are tertiary amines also may be used, but not necessarily with equivalent results. The strong anion exchange resins which are used in the preferred embodiment of our invention usually are based on a quaternary benzylic ammonium compound as represented by polystyrene and non-polystyrene gel resins with the group $ArCH_2N^+(CH_3)_3$, polystyrene gel-type resins with the group ArCH$_2$N+(CH$_3$)$_2$(CH$_2$CH$_2$OH), and macroreticular resings of each of the foregoing structures, where Ar is an aromatic ring or some portion thereof, usually benzene. The characteristic of importance in our invention is that the resin have anion exchange sites which can be exchanged with molybdate or a molybdate precursor.

The anion exchange resin is exchanged with a molybdate to afford at least 5 weight percent, and most often from between 5 to about 30 weight percent, molybdenum in the final product. The amount of molybdate on the exchanged resin primarily affects the productivity of the process, i.e., the amount of aldose which can be epimerized per unit time, but does not affect the nature of this process. Consequently, it can be said fairly that the amount of molybdenum on the exchanged resin is not critical to the success of our invention, and is largely a matter of choice. The exchange may be effected by any soluble oxoanion of Mo(VI) whose solubility in aqueous solution is at least 100 ppm at some point within the pH range of 0.1–6.0. Molybdate salts, i.e. salts of the MoO$_4$ dianion, are most commonly employed in the exchange, and include the molybdate salts of sodium, potassium, lithium, calcium, strontium, zinc, iron(II), magnesium, ammonium, and barium. Organo-metallic molybdates complexes, such as molybdenum(VI) oxide bis(2,4-pentanedionate) also may be used in the practice of this invention, as well as molybdenum trioxide which usually is considered a water-insoluble material but whose solubility is sufficient to satisfy the criteria articulated above. Exchange can, in fact, be affected by any molybdenum species which after being placed on an exchangeable site in an anion exchange resin is convertible to a molybdenum(VI) oxy anion.

The exchange may be performed in either a batch or continuous mode, normally at or near room temperature although temperatures up to 100° C. can be used. In a typical exchange, a mixture of the resin and a 20 weight percent solution of sodium molybdate may be mixed at room temperature at a pH between about 0.5 and about 6.0 for a period up to 2 days to incorporate up to about 30% by weight molybdenum.

The pH at which the exchange is effected has an important influence on the activity and stability of the resulting solid catalyst and is in the range from 0.1 to about 6.0. Quite typically exchange needs to be effected at a pH no more than about 6.0 in order to obtain an active epimerization catalyst. Exchange usually will be conducted at a pH between about 0.1 and 4.0, and even more often between about 0.5 and about 2.5. The particular pH ranges which are optimum for any particular catalyst vary with the resin but can be readily determined through simple experimentation. However, it has been observed that in general exchange at a lower pH tends to afford a more stable resin, i.e., one which shows decreased deactivation upon continued use. That is, the stability of the solid catalysts appears to be somewhat greater when catalysts are prepared in the lower pH range than when prepared at a higher pH.

The solid catalysts contain molybdenum at a level between about 5 and about 30 weight percent elemental molybdenum based on dry weight of finished catalyst, and more usually contain between about 10 and about 25 weight percent molybdenum. The particular level of molybdenum in the finished solid catalyst depends upon the nature of the resin, the amount of molybdate offered in exchange, the pH of the exchange, and so on. Molybdenum level has an effect on the epimerization process, e.g., on productivity, but it is not critical element in the success of our invention.

An important feature of the catalysts of our invention which makes a key contribution to the design of a continuous epimerization process is the low level of molybdenum leach during their use under reaction conditions. It is clear that a high level of molybdenum leach is unacceptable on at least two counts. Since molybdenum is the active species in epimerization, its loss from the solid catalyst can be expected to be accompanied by a loss of catalytic activity. Therefore significant molybdenum leach will lead to accelerated catalyst deactivation. Where high levels of molybdenum are present in the product solution of epimerized aldose or aldose analog molybdenum needs to be removed prior to an aldose separation stage. Therefore, significant molybdenum leach will necessitate an added purification stage in producing the epimeric product. The process of our invention is characterized by a molybdenum leach of less than about 50 ppm molybdenum under epimerization conditions, frequently under about 25 ppm, and often under about 15 ppm.

The solid catalysts prepared as described have several quite favorable characteristics. The catalysts are highly selective in catalyzing the epimerization of aldose or aldose analogs. By selective we mean that the reactant aldose is converted to its epimer with minimal formation of by-products. The solid catalysts are also quite stable and can be used in continuous operation for periods in excess of 150 hrs. Depending upon their mode of preparation, some catalysts show virtually no change in activity through at least 320 hours. Using as a standard the epimerization of mannose at 95° C. performed at a liquid hourly space velocity sufficient to afford at least 25% of the equilibrium value of glucose, the catalysts of our invention generally show a deactivation under about 10% per day in a continuous process, which corresponds to a half life of at least about 160 hours. The solid catalysts can be prepared well ahead of time and stored without substantial degradation of loss in activity.

Epimerization with a solid catalyst of this invention usually is performed in a temperature range between about 40° and 110° C., but more usually in the interval between about 70° and about 100° C., and even more commonly between about 80° and about 95° C. The most important effect of temperature appears to be the rate of epimerization, and consequently a temperature will be chosen so as to afford a convenient reaction rate. On the other hand the operating temperature also may effect the structural and chemical stability of the catalyst itself, which can be a consideration, at least occasionally, in choosing an appropriate reaction temperature. The time over which epimerization is conducted will be quite variable depending upon the reaction temperature, the particular solid catalyst used, the amount of molybdenum contained in the catalyst, the extent of conversion sought, and so forth. Frequently it is not commercially desirable to conduct the reaction to equilibrium, since the time to reach equilibrium may be inordinately long relative to the time necessary to reach, say, 80% of the equilibrium value. Consequently epimerization will be run for a time sufficient to achieve a commercially acceptable product distribution. As a practical matter the reaction generally will be run for a time sufficient to achieve at least one-quarter and more usually at least one-half of the equilibrium value of the desired epimer.

Epimerization may be performed either in a batch mode or, preferably, in a continuous mode. In a batch mode the solid catalyst is mixed with an aqueous solution containing the aldose or aldose analog to be epimerized at a pH between about 1 and about 6, but usually in the pH region from about 4.0 to about 6.0, and at a temperature between about 40° and about 110° C. for a time sufficient to afford the desired proportion of the epimer wanted. The solid catalyst is then removed, as by filtration, with the filtrate being the reaction product. The epimeric pair may be used without further processing, although generally one or both of the epimeric pair is separated in purer form by appropriate means, as by chromatography.

The solid catalysts of this invention are more efficiently used in a continuous process for the epimerization of aldose or aldose analogs. One skilled in the art will recognize that many variations are possible, and the following description is merely representative of these variations. The molybdate exchange resin which is the solid catalyst of this invention most often will be used as a packed bed but also may be used as a fluidized bed or ebullated bed. The feedstock is an aqueous solution of an aldose or aldose analog optionally containing other additives at a pH between about 1 and 6. In a preferred mode the pH of the aqueous aldose or aldose analog feedstock will be that indigenous to its solution and be within the range between 4.0 and 6.0. The aqueous feedstock is then passed upflow or downflow through the packed bed at a liquid hourly space velocity which will depend upon the reaction temperature, the amount of molybdenum in the solid catalyst, and the degree of epimerization sought. So, for example, wit a catalyst containing between about 10 and 20 weight percent molybdenum operating on a 10 weight percent mannose aqueous solution at 95° C., a liquid hourly space velocity of 1-2 affords approximately equilibrium values of the epimeric mannose-glucose pair during initial use of the bed. The resin does exhibit deactivation with use but its time dependence depends upon the resin, the nature and concentration of aldose feedstock, and the amount of molybdenum exchanged, as well as the pH of molybdenum exchange. However, in a more-or-less typical case a catalyst acting on 10% mannose as the feedstock at 95° C. and at a liquid hourly space velocity to initially give the equilibrium concentration of glucose in the epimerized product after 150 hrs. on stream at the same liquid hourly space velocity of feedstock affords about one-half the equilibrium value of glucose.

The examples which follow are only illustrative of our invention and are merely representative of the many embodiments subsumed within our invention. In particular, our invention is not to be limited in any way by the examples.

EXAMPLES I–VIII

A solid molybdate catalyst on a basic, anion exchange resin was prepared as follows: Into a 500 mL Erlenmeyer flask were placed 50.0 g of sodium molybdate dihydrate and 200 mL of deionized water. The mixture was stirred until a solution was obtained, then the pH of the solution was adjusted to 4.0 by the careful addition of concentrated sulfuric acid. To the resulting acidified molybdate solution were then added 50.0 g of Rohm & Haas Amberlite IRA-400, which is a strongly basic polystyrene gel type ion exchange resin of the quaternary benzyl ammonium type, in the chloride form. The flask was stoppered and remained at room temperature for two days, with occasional gentle swirling. The resulting solid catalyst was collected on a glass frit funnel. In order to completely remove all unexchanged molybdate, the solid catalyst was washed with portions of deionized water totaling 3L. The washed catalyst was then ready for use. A sample of the solid catalyst was dried under vacuum at 60° C. for 5 hours, then analyzed. The resin was found to contain 20.7 weight percent molybdenum.

The above process was repeated, varying the basic anion exchange resin used and the pH of the aqueous molybdate solution, as summarized in Table 1.

TABLE 1

Molybdate-exahanged Anion Exchange Resins

| Example No. | Resin | Type | Exchange pH | Weight % Mo Found |
|---|---|---|---|---|
| 1 | Amberlite IRA-400$^a$(Cl) | G | 4.0 | 20.7 |
| 2 | Amberlite IRA-400$^a$(Cl) | G | 1.0 | 13.7 |
| 3 | Amberlite IRA-400$^a$(Cl) | G | 9.75 | 6.07 |
| 4 | Amberlyst A-27$^b$ | M | 4.0 | 20.2 |
| 5 | Amberlyst A-27$^b$ | M | 9.75 | 6.3 |
| 6 | Amberlite IRA-47$^c$ | G | 4.0 | 20.3 |
| 7 | Amberlite IRA-47$^c$ | G | 7.4 | 13.4 |
| 8 | Amberlite IRA-400$^a$(OH) | G | 1.0 | 20.9 |

G = Gel
M = macroreticular
$^a$Strongly basic polystyrene anion exchange resin of quaternary benzyl ammonium type.
$^b$Strongly basic macroporous anion exchange resin quaternary benzyl ammonium type.
$^c$Intermediate basic resin of tertiary amine type.

EXAMPLE IX–XVI

The following general method was used to evaluate the catalytic activity and stability toward leaching of the solid catalysts prepared in Examples I–VIII. A 1cc sample of solid catalyst was mixed in a test tube with 6.0 mL of a 9.1 weight percent aqueous solution of D-mannose. The test tube was stoppered and shaken at 80° C. typically for 24 hours. Sample aliquots were typically removed after 2,4,6,8,18 and 24 hours and were analyzed by HPLC to determine the extent of epimerization of D-mannose to D-glucose. Active catalysts yielded equilibrium mixtures (~70% glucose: ~30% mannose) after about 4–8 hours. Inactive catalysts either showed no epimerization activity at all, or failed to achieve equilibrium mixtures even after 24 hours. Aliquots removed after 24 hours were also submitted for AAS analysis to determine the levels of molybdenum leached into the solutions from the solid catalysts. The pH of the reaction mixtures remained at $\leq 5.3$ throughout the reaction period. The evaluations are summarized in Table 2.

TABLE 2

| Example No. | Resin | Preparation pH | Catalytic Activity | 24 hr. Leach Level (ppm Mo) |
|---|---|---|---|---|
| 9 | Amberlite IRA-400(Cl) | 4.0 | + | 6 |
| 10 | Amberlite IRA-400(Cl) | 1.0 | + | 11 |
| 11 | Amberlite IRA-400(Cl) | 9.75 | − | 2 |
| 12 | Amberlyst A-27 | 4.0 | + | 9 |
| 13 | Amberlyst A-27 | 9.75 | − | N.D. |
| 14 | Amberlite IRA-47 | 4.0 | + | 34 |
| 15 | Amberlite IRA-47 | 7.4 | − | 124 |
| 16 | Amberlite IRA-400(OH) | 1.0 | + | 31 |

N.D. = Not Determined

EXAMPLES XVII–XXI

In order to demonstrate that the catalytic activity exhibited by the solid catalysts prepared in Examples I–VIII above results from molybdate which is anion exchanged (i.e., which is ionically bonded to sites on the basic anion exchange resins) and not merely adsorbed on the solid surface or physically entrapped, attempts were made to prepare solid catalysts using acidic, cation exchange resins in which anion exchange is impossible. The process of Example I was used in attempting to prepare these catalysts, the only difference being that acidic, cation exchange resins were used here in place of the basic, anion exchange resins. The process of Examples IX–XVI was used to evaluate the activity of these solid catalysts pepared on acidic, cation exchange resins. The results of these evaluations appear in Table 3.

TABLE 3

| Example No. | Resin | Type | Preparation pH | ppm Mo Found | Catalytic Activity |
|---|---|---|---|---|---|
| 17 | Amberlite IR-118(H) | G | 2.0 | 145 | none |
| 18 | Amberlite IR-118(H) | G | 0.2 | 202 | none |
| 19 | Amberlite 200(H) | M | 2.0 | 87 | none |
| 20 | Amberlite 200(Na) | M | 1.9 | 91 | none |
| 21 | Amberlite IRC-50(H) | M | 2.0 | 588 | none |

G = Gel
M = Macroreticular

From these results it is obvious that only very low levels of molybdate are adsorbed and/or entrapped in the resins. Therefore, the high(>10 weight percent) levels of molybdenum found in the solid catalyst prepared using basic, anion exchange resins necessarily must represent ionically bonded (exchanged) molybdate. Also, it is obvious from these results that the low (<100 ppm) levels of molybdenum leached from the solid catalysts in Examples IX–XVI are too low to account for their observed catalytic activity.

EXAMPLE XXII

Continuous epimerization of mannose: Catalyst A. A feedstock of 10 weight percent aqueous D-mannose (pH Ca. 5) was passed upflow through a fixed bed of catalyst (23 cc) at a temperature of 90° C. The catalyst was a macroreticular anion exchange resin (Amberlist™27) exchanged with sodium molybdate at pH 4.0 which was subsequently washed with water to remove all nonexchanged molybdate. The catalyst had 20.2 weight percent molybdenum and the feedstock was passed upflow at a constant rate of 6.5 cc per hr. per g of molybdenum, corresponding to 0.65 cc of feedstock per cc of catalyst per hour (0.65 LHSV). Effluent was analyzed for glucose, mannose, and molybdenum content with the results being summarized in Table 4 and FIG. 1.

TABLE 4

| | Continuous Epimerization of Mannose | | |
|---|---|---|---|
| Hrs. on stream | Glucose | Mannose | Mo ppm |
| 4 | 54.8 | 43.0 | 8.2 |
| 8 | 57.0 | 40.6 | |
| 20 | 48.5 | 49.5 | 11 |
| 28 | 43.7 | 53.7 | |
| 32 | 44.0 | 53.7 | 12 |
| 44 | 41.5 | 56.9 | |
| 52 | 40.8 | 57.1 | 17 |
| 60 | 39.6 | 58.1 | |
| 68 | 38.9 | 59.3 | 22 |
| 76 | 38.0 | 60.0 | |
| 84 | 28.2 | 70.2 | 20 |
| 92 | 36.6 | 61.5 | 24 |
| 96 | 36.1 | 62.1 | |
| 104 | 36.6 | 61.2 | |
| 108 | 35.9 | 62.2 | |
| 116 | 34.8 | 63.3 | 26 |
| 124 | 34.8 | 64.1 | |
| 132 | 32.8 | 65.1 | |
| 140 | 32.8 | 65.5 | 28 |
| 148 | 30.6 | 67.9 | |
| 156 | 30.1 | 68.5 | 28 |
| 164 | 28.8 | 69.2 | |

EXAMPLE XXIII

Figure 2:
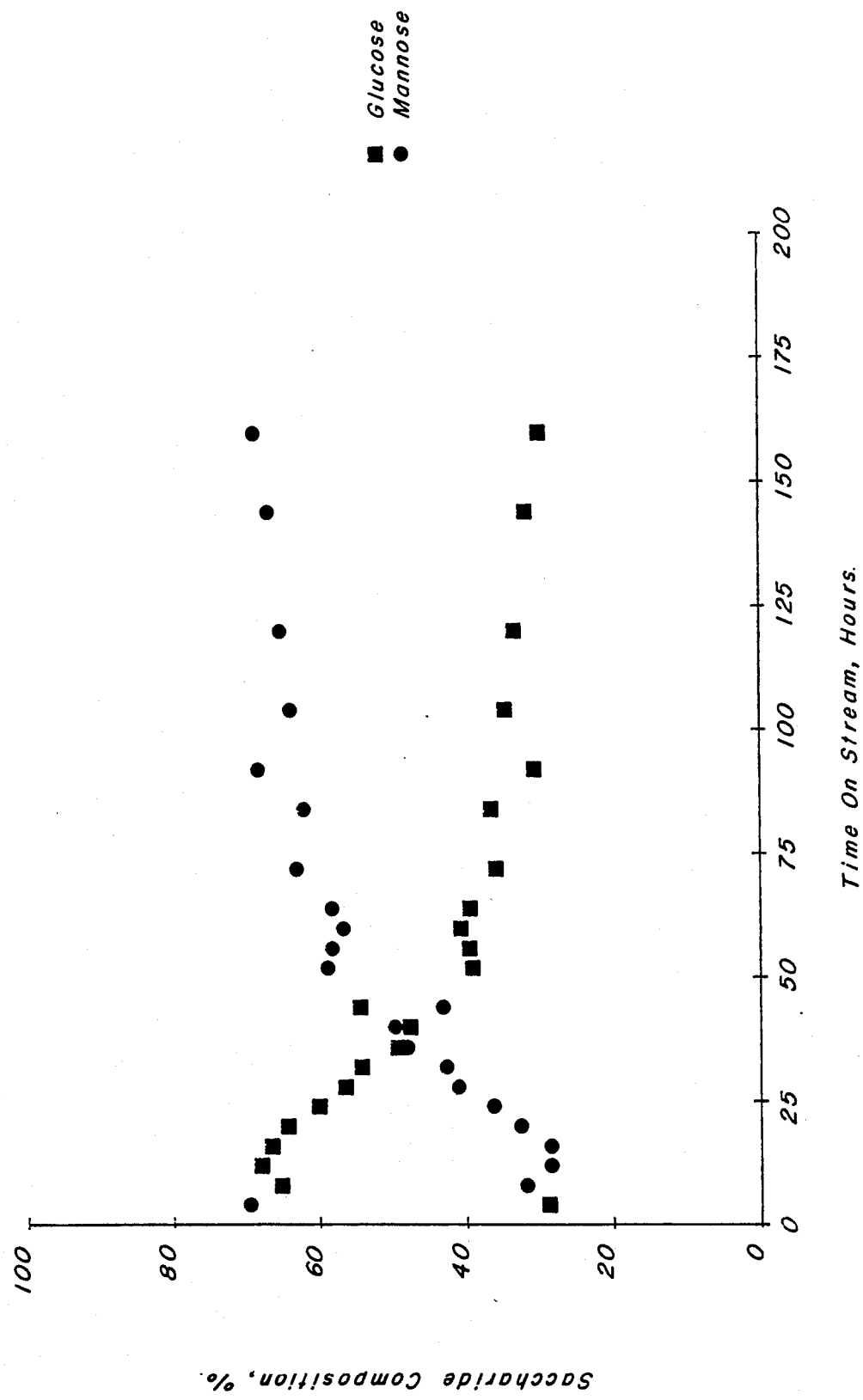
FIG. 2 is a graphical representation of the continuous epimerization of mannose of Example XXII.

Continuous epimerization of mannose: Catalyst B. A 10% feedstock of mannose (pH ca.5) was continuously epimerized by passing the feedstock upflow at a rate of 9 cc per hr. per g of molybdenum (LHSV of 1.0) on the solid catalyst at 95° C. The catalyst was a fixed bed of 11 cc of a gel-type anion exchange resin (IRA-400) exchanged with sodium molybdate at pH 4.0 to afford a catalyst containing 22.1 weight percent molybdenum. The results are summarized in the following table and depicted in FIG. 2.

TABLE 5

| | Continuous Epimerization of Mannose | | |
|---|---|---|---|
| Hrs. on stream | Glucose | Mannose | Mo ppm |
| 4 | 28.8 | 69.7 | 1.2 |
| 8 | 65.2 | 31.9 | 3.2 |
| 12 | 68.0 | 28.6 | 5.0 |
| 16 | 66.5 | 28.6 | 6.0 |
| 20 | 64.3 | 32.7 | 5.2 |
| 24 | 60.0 | 36.4 | |
| 28 | 56.4 | 41.2 | |
| 32 | 54.2 | 42.8 | 3.6 |
| 36 | 49.3 | 48.1 | |
| 40 | 47.6 | 49.8 | |
| 44 | 54.4 | 43.2 | 2.3 |
| 52 | 39.0 | 58.9 | |
| 56 | 39.5 | 58.3 | 1.0 |
| 60 | 40.7 | 56.8 | |
| 64 | 39.4 | 58.3 | 1.0 |
| 72 | 35.8 | 63.1 | 1.5 |
| 84 | 36.5 | 62.1 | 1.9 |
| 92 | 30.6 | 68.3 | 1.9 |
| 104 | 34.5 | 63.9 | 2.4 |
| 120 | 33.2 | 65.2 | 1.9 |

TABLE 5-continued

| Continuous Epimerization of Mannose | | | |
|---|---|---|---|
| Hrs. on stream | Glucose | Mannose | Mo ppm |
| 144 | 31.6 | 66.8 | 1.8 |
| 160 | 29.7 | 68.7 | |

EXAMPLE XXIV

Figure 3:
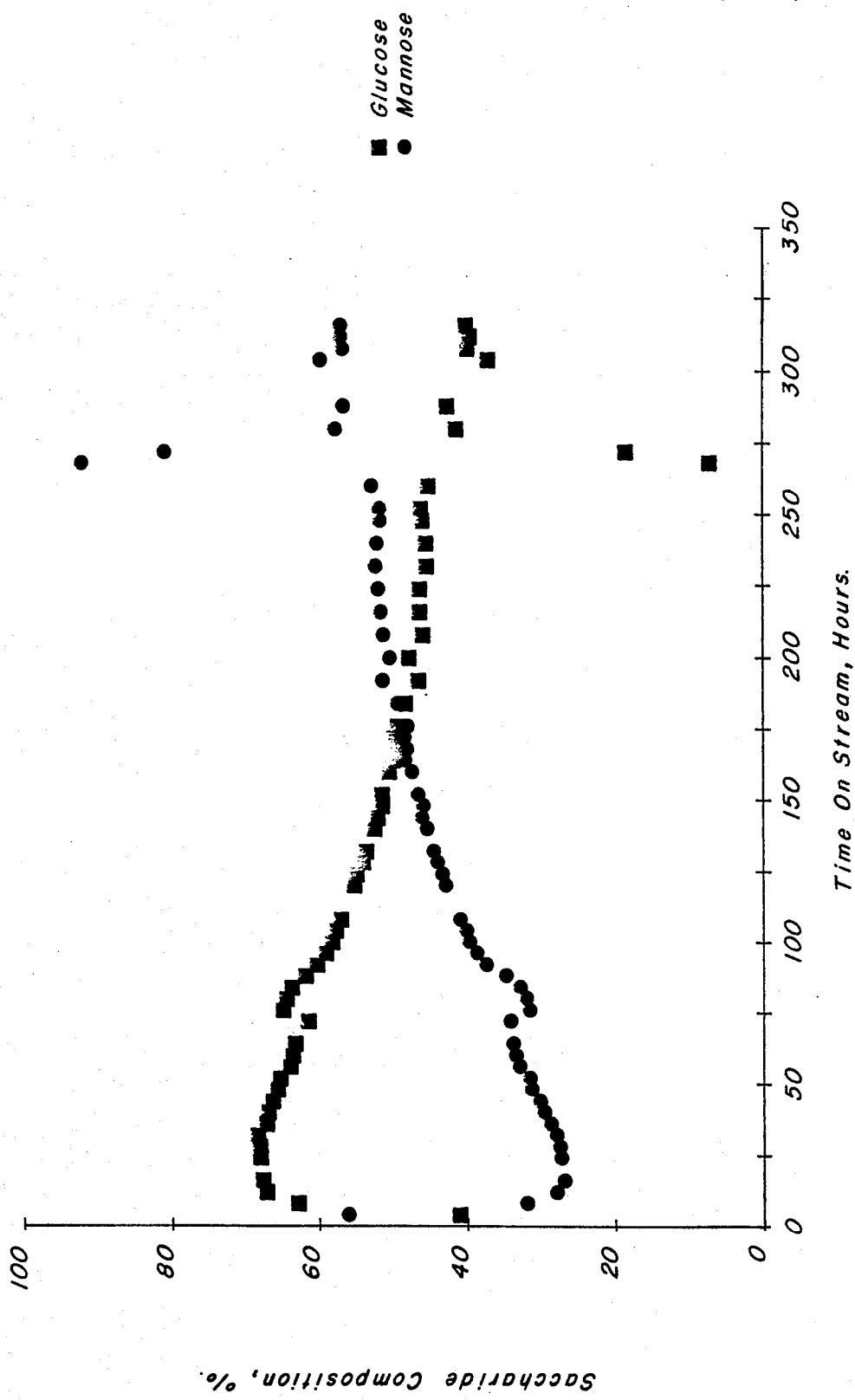
FIG. 3 is a graphical representation of the continuous epimerization of mannose of Example XXIV.
Figure 4:
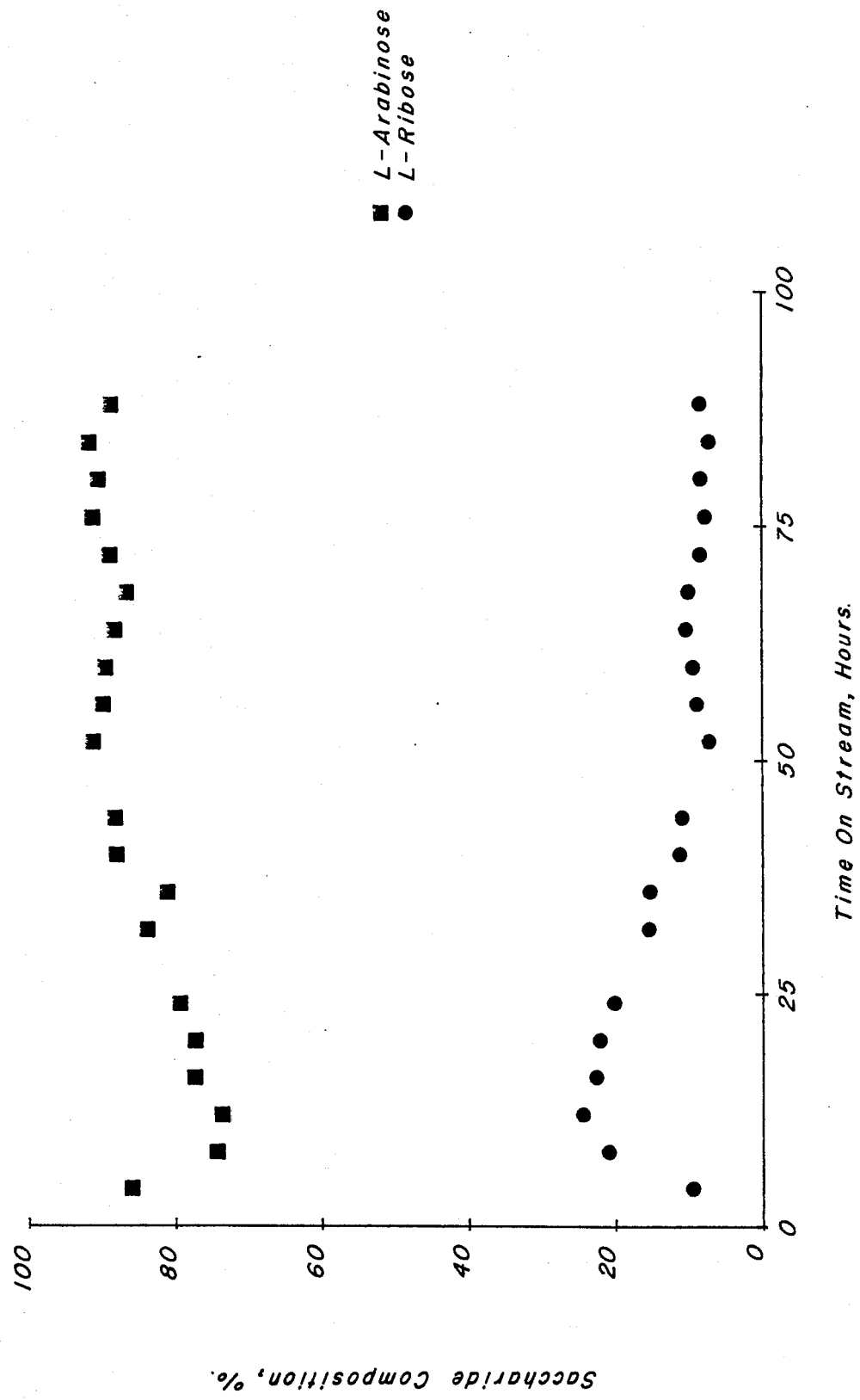
FIG. 4 is a graphical representation of the continuous epimerization of L-arabinose of Example XXV.

Continuous Epimerization of D-Mannose: Catalyst 3. Twenty grams of Amberlite$^{TM}$IRA-400 (CI$^-$) was mixed with 100 mL of 17 weight percent Na$_2$MoO$_4$.2-H$_2$O solution and adjusted to pH 0.52 with concentrated H$_2$SO$_4$. The mixture was allowed to stand for several days after which the resin was separated by filtration and was washed thoroughly with 5 L of deionized H$_2$O. The finished catalyst was found to contain 13.1% Mo. This catalyst (17 cc) was placed in a vertical column reactor fitted with a heating jacket. A 10% D-mannose feed was pumped upflow through the catalyst at 20 cc/hr (1.2 LHSV). Products were collected at 4 hr. intervals and analyzed with the composition of each product period given below. Comparison of these data with those of Example XXIII show the increased stability attending catalyst preparation at a lower pH. Results are also portrayed in FIG. 3.

TABLE 6

| Continuous Epimerization of Mannose | | | |
|---|---|---|---|
| Hrs. on stream | Glucose | Mannose | Mo ppm |
| 4 | 41.0 | 56.2 | 14 |
| 8 | 62.8 | 32.0 | |
| 12 | 67.1 | 28.0 | |
| 16 | 67.6 | 27.0 | |
| 24 | 68.0 | 27.4 | 10 |
| 28 | 68.1 | 27.6 | |
| 32 | 68.3 | 28.0 | |
| 36 | 67.1 | 28.8 | 5.2 |
| 40 | 66.9 | 29.6 | |
| 44 | 66.3 | 30.2 | |
| 48 | 65.6 | 31.3 | 3.3 |
| 52 | 65.2 | 31.6 | |
| 56 | 63.9 | 33.0 | |
| 60 | 63.5 | 33.5 | 2.5 |
| 64 | 63.2 | 33.8 | |
| 72 | 61.4 | 34.2 | |
| 76 | 64.8 | 31.6 | 4.8 |
| 80 | 64.3 | 32.0 | |
| 84 | 63.6 | 32.9 | |
| 88 | 61.7 | 34.8 | |
| 92 | 60.2 | 37.4 | 2.5 |
| 96 | 59.0 | 38.7 | |
| 100 | 58.1 | 39.6 | |
| 104 | 57.6 | 40.1 | |
| 108 | 56.9 | 40.9 | 1.9 |
| 120 | 55.1 | 42.9 | |
| 124 | 54.8 | 43.3 | |
| 128 | 53.9 | 44.0 | |
| 132 | 53.5 | 44.5 | |
| 140 | 52.4 | 45.4 | |
| 144 | 52.0 | 46.1 | |
| 148 | 51.4 | 45.9 | |
| 152 | 51.4 | 46.6 | |
| 160 | 50.4 | 47.4 | |
| 164 | 49.8 | 48.4 | |
| 168 | 49.7 | 48.1 | |
| 172 | 49.8 | 48.5 | |
| 176 | 49.2 | 48.0 | |
| 184 | 48.2 | 49.4 | 1.2 |
| 192 | 46.4 | 51.4 | |
| 200 | 47.7 | 50.4 | |
| 208 | 45.8 | 51.3 | |
| 216 | 46.2 | 51.6 | 1.1 |
| 224 | 46.2 | 52.0 | |
| 232 | 45.3 | 52.3 | |
| 240 | 45.4 | 52.1 | 1.1 |
| 248 | 45.9 | 51.7 | 1.4 |

TABLE 6-continued

| Continuous Epimerization of Mannose | | | |
|---|---|---|---|
| Hrs. on stream | Glucose | Mannose | Mo ppm |
| 252 | 46.1 | 51.8 | |
| 260 | 45.0 | 52.8 | |
| 268 | 7.1 | 92.0 | |
| 272 | 18.4 | 80.8 | |
| 280 | 41.3 | 57.7 | 1.3 |
| 288 | 42.5 | 56.6 | |
| 304 | 36.9 | 59.7 | |
| 308 | 39.7 | 56.7 | 1.2 |
| 312 | 39.4 | 56.9 | |
| 316 | 39.9 | 56.9 | 1.1 |

EXAMPLE XXV

Continuous Epimerization of L-Arabinose: Catalyst 4. Twenty grams of Amberlite$^{TM}$ IRA-400 (C1) ion-exchange resin was mixed with 100 mL of 17 weight percent Na$_2$MoO$_4$.2H$_2$O solution and adjusted to pH 4.0 with concentrated H$_2$SO$_4$. The mixture was agitated for 20 hrs. and then filtered to remove the resin from the molybdate solution. The resin was then washed thoroughly with 5 L of deionized water to remove excess molybdate. The finished catalyst was found to contain 11.5 weight percent elemental Mo. This catalyst (16.5 cc) was loaded into a vertical tube reactor fitted with a heating jacket, which was maintained at approximately 95° C. A 10% aqueous L-arabinose feed (pH ca.5) was pumped upflow at 20 cc hr. (1.2 LHSV) over the catalyst. Products were collected at 4 hr. intervals and were analyzed. The composition of each product period are given below.

TABLE 7

| Continuous Epimerization of L arabinose | | | |
|---|---|---|---|
| Hrs. on Stream | % L-Arabinose | % L-Ribose | Mo ppm |
| 4 | 86.0 | 9.6 | 6.5 |
| 8 | 74.3 | 21.0 | |
| 12 | 73.6 | 24.5 | 15 |
| 16 | 77.3 | 22.7 | |
| 20 | 77.2 | 22.2 | 8 |
| 24 | 79.3 | 20.2 | |
| 32 | 83.7 | 15.5 | |
| 36 | 81.0 | 15.3 | 4.5 |
| 40 | 87.9 | 11.3 | |
| 44 | 88.1 | 11.0 | 3.5 |
| 52 | 91.1 | 7.3 | |
| 56 | 89.7 | 8.9 | 2.5 |
| 60 | 89.4 | 9.4 | |
| 64 | 88.1 | 10.4 | |
| 68 | 86.5 | 10.0 | |
| 72 | 88.7 | 8.4 | |
| 76 | 91.0 | 7.7 | |
| 80 | 90.2 | 8.3 | 4.0 |
| 84 | 91.4 | 7.2 | |
| 88 | 88.4 | 8.4 | |

In a similar fashion an aqueous solution of L-rhamnose may be epimerized to a mixture containing L-rhamnose and L-6-deoxyglucose.

EXAMPLE XXVI

Figure 5:
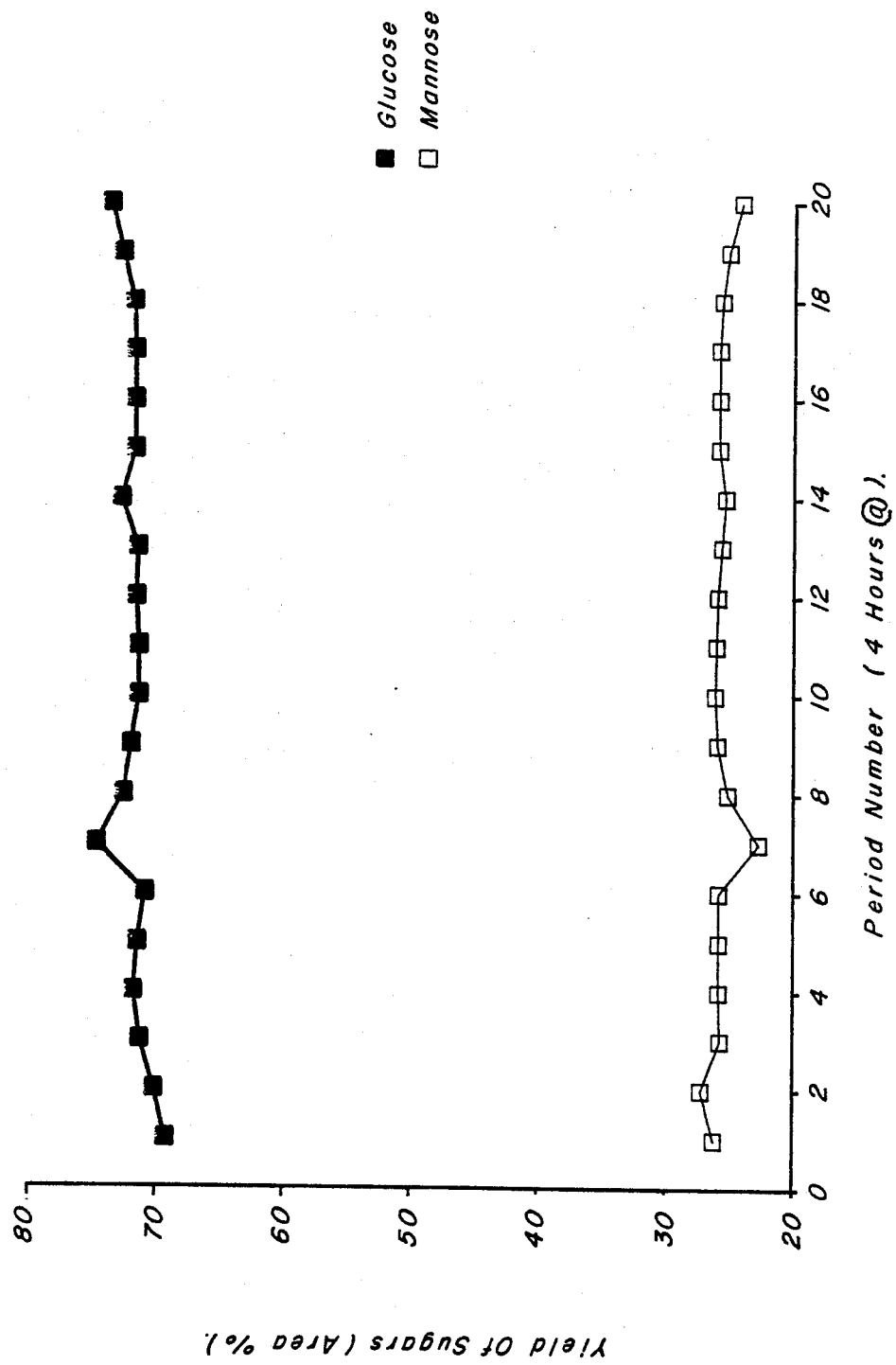
FIG. 5 is a graphical representation of the continuous epimerization of a commercial starch hydrolysate (Example XXVI).

A commercial starch hydrolysate at pH 5.3 containing 96% glucose, 2.3% other disaccharides, and 1.4% higher polysaccharides was diluted to 10 weight percent glucose and used as a feedstock for an epimerization catalyst prepared from Amberlite IRA-400 ion exchange resin and sodium molybdate at pH 1.0 and containing 15.9 weight percent molybdenum. The feedstock was passed at 1 LHSV over the catalyst at 60°–70° C. to give the results shown in FIG. 5. This figure clearly shows virtually no loss in activity after 80 hours where the product contains 23-28% mannose (approximately 87% of the equilibrium value).

What is claimed is:

1. A method of epimerizing an aldose comprising flowing an aqueous solution of said aldose under epimerizing conditions through a bed of a molybdate exchanged anion exchange resin at a liquid hourly space velocity sufficient to achieve at least one quarter of the equilibrium value of the epimer and recovering the resulting epimerized product mixture,, where said anion exchange resin is exchanged with a molybdate compound at a pH between about 0.1 and about 4.0 so as to contain molybdenum at its anion exchange sites in an amount at least about 11.5% by weight molybdenum based on said anion exchanged resin and where the molybdate exchanged resin is further characterized by a molybdenum leach level less than about 50 ppm under said epimerizing conditions and a half life of at least about 160 hours at 95° C.

2. The method of claim 1 where the epimerizing conditions include a temperature between about 40° and about 110° C.

3. The method of claim 2 where the epimerizing conditions include a temperature between 70° and 100° C.

4. The method of claim 3 where the epimerizing conditions include a temperature between 80° and 95° C.

5. The method of claim 1 where the molybdate is an oxoanion of molybdenum(VI) soluble to the extent of at least 100 ppm at a point within the pH region between 0.1 and 6.0.

6. The method of claim 5 where the molybdate is a salt of the $MoO_4$ dianion.

7. The method of claim 6 where the molybdate is a salt of sodium, potassium, lithium, calcium, strontium, zinc, iron(II), magnesium, ammonium, or barium.

8. The method of claim 1 where the aldose is selected from the group consisting of ribose, arabinose, xylose, lyxose, allose, altrose, glucose, mannose, gulose, idose, galactose, and talose.

9. The method of claim 8 where the aldose is arabinose.

10. The method of claim 8 where the aldose is mannose.

11. The method of claim 1 where the aldose is L-mannose and the epimerized mixture contains L-mannose and L-glucose.

12. The method of claim 1 further characterized in that the epimerized product mixture contains less than about 50 ppm molybdenum.

13. The method of claim 12 where the mixture contains less than about 25 ppm molybdenum.

14. The method of claim 13 where the mixture contains less than about 15 ppm molybdenum.

15. The method of claim 1 where said epimerizing conditions include a pH for the aqueous solution of said aldose of about 1 to about 6.

16. The method of claim 15 where said epimerizing conditions include a pH between about 4 and about 6.

* * * * *